(12) United States Patent  
Norton

(10) Patent No.: US 7,081,957 B2
(45) Date of Patent: Jul. 25, 2006

(54) APERTURE TO REDUCE SENSITIVITY TO SAMPLE TILT IN SMALL SPOTSIZE REFLECTOMETERS

(75) Inventor: Adam E. Norton, Palo Alto, CA (US)

(73) Assignee: Therma-Wave, Inc., Fremont, CA (US)

( * ) Notice: Subject to any disclaimer, the term of this patent is extended or adjusted under 35 U.S.C. 154(b) by 308 days.

(21) Appl. No.: 10/820,903

(22) Filed: Apr. 8, 2004

(65) Prior Publication Data

US 2005/0225767 A1    Oct. 13, 2005

(51) Int. Cl.
   *G01N 21/55*    (2006.01)
   *G01J 1/42*     (2006.01)
(52) U.S. Cl. ...................... 356/445; 250/372
(58) Field of Classification Search ........ 356/445–448, 356/326–328, 372
   See application file for complete search history.

(56) References Cited

U.S. PATENT DOCUMENTS 5,486,701 A    1/1996  Norton et al. .............. 250/372
5,747,813 A    5/1998  Norton et al. .............. 250/372
2004/0113043 A1*  6/2004  Ishikawa et al. .......... 250/201.4

* cited by examiner

*Primary Examiner*—Layla G. Lauchman
*Assistant Examiner*—Amanda Merlino
(74) *Attorney, Agent, or Firm*—Stallman & Pollock LLP

(57) ABSTRACT

An aperture for reducing tilt sensitivity in normal incidence optical metrology is formed to include one or more holes. The aperture is positioned to partially occlude one-half of the pupil of a normal incidence objective. A probe beam is projected to fill the pupil of the objective. The portion of the incident probe beam that passes through the aperture is reduced in cross-sectional profile. As a result, after reflection by the sample, that portion of the probe beam underfills the non-occluded portion of the pupil. The portion of the incident probe beam that passes through the non-occluded portion of the pupil overfills the occluded pupil upon reflect by the sample. The combination of underfilling and overfilling reduces the sensitivity of the objective to tilting of the sample.

8 Claims, 3 Drawing Sheets

APERTURE TO REDUCE SENSITIVITY TO SAMPLE TILT IN SMALL SPOTSIZE REFLECTOMETERS

TECHNICAL FIELD

This invention relates to optical tools for measuring and evaluating semiconductor wafers. In particular, the present invention relates to methods for reducing the sensitivity of metrology tools to sample tilt present during the measurement process.

BACKGROUND OF THE INVENTION

As semiconductor geometries continue to shrink, manufacturers have increasingly turned to optical techniques to perform non-destructive inspection and analysis of semiconductor wafers. Techniques of this type, known generally as optical metrology, operate by illuminating a sample with an incident field (typically referred to as a probe beam) and then detecting and analyzing the reflected energy. Ellipsometry and reflectometry are two examples of commonly used optical techniques. For the specific case of ellipsometry, changes in the polarization state of the probe beam are analyzed. Reflectometry is similar, except that changes in intensity are analyzed.

As shown in FIG. 1, a typical reflectometer includes an illumination source that creates a monochromatic or polychromatic probe beam. The probe beam is projected by one or more lenses onto the surface of a sample. The sample reflects the probe beam and the reflected probe beam (or a portion of the reflected probe beam) is transported to a detector. The detector transforms the energy it receives into corresponding output signals. A processor analyzes the signals to measure the structure or composition of the sample. Reflectometers are often used to measure film thickness and dimensions of etched lines among other properties on semiconductor wafers. Instruments such as these that are designed to measure small spots on specular samples at near-normal incidence will usually use a microscope objective both to focus illumination onto the sample and to collect the reflected light.

An issue with this arrangement is that it can cause the measurements to be sensitive to small errors in local sample tilt. This effect is shown in FIGS. 2 and 3. FIG. 2 shows the typical shape of the pupil of a reflective Schwarzschild microscope objective often used in reflectometers. A cross-section of a portion of a reflectometer containing the objective is shown in FIG. 3. Illumination light 302 reflects from beamsplitter 304 and illuminates the entire objective pupil shown schematically as 306. The light that passes through the pupil is shown as the shaded area 308. This light is focused by the objective shown schematically as 310. The light reflects off a small area of the sample 312 and returns through the objective 310 and pupil 306. Light that passes through the left side of the pupil 306 heading towards the sample 312 will return through the right side and vice versa. The returning light arrives at the beamsplitter 304 where a portion is transmitted. It then continues to a detector (not shown) where at least a portion of the light is collected and measured. In the case of the typical symmetric pupil shown in FIG. 3, the light returning from the sample 312 has the same width as the opening in the pupil through which is must pass. A problem with this typical arrangement is that small variation in sample tilt will cause an undesired variation in the amount of light collected by the detector and therefore degrade the reproducibility of the measurements.

One effective solution to minimize this sensitivity to sample tilt is to place an aperture in the illumination path before the beamsplitter that has openings smaller than those in the objective pupil. A lens may be used to project this aperture onto the back focal plane of the objective to insure good telecentricity. The main drawback with this approach is that it becomes complicated to accommodate multiple objectives, mounted in a turret for example, that may be used in the instrument. A different aperture may be needed for each one. A fixed aperture in the illumination path may also interfere with other configurations of the instrument. It would be very desirable to have a solution for the tilt sensitivity that did not affect other objectives or instrument configurations.

Another problem that is peculiar to the type of pupil shown in FIG. 2 is that the straight "spider arms" that join the central obstruction to the outside diffract light in the vertical and horizontal directions and make it more difficult to measure very small areas on the wafer.

To minimize this type of tilt sensitivity, U.S. Pat. No. 5,486,701 and U.S. Pat. No. 5,747,813 discloses the use of a fully-reflecting mirror covering half the objective pupil together with an aperture to create a beam of illumination that enters only one half of the pupil and exits only from the other half where it can be either slightly larger or smaller than the exit opening. This patent does not disclose how the tilt sensitivity might be remedied when a conventional partially reflecting beam splitter is used to direct light down both halves and collect light from both halves.

For at least these reasons, a need exists for a method for reducing the sensitivity of Schwarzschild (and other normal incidence) objectives to sample tilt. Methods of this type are particularly relevant for metrology systems that use multiple objectives mounted on a single turret. Preferably, such methods would be retrofittable to existing systems and work in combination with traditional beam splitters (i.e., beam splitter that cover the entire objective pupil).

SUMMARY OF THE INVENTION

The present invention includes an aperture for reducing tilt sensitivity in normal incidence optical metrology. The aperture is formed to include one or more holes and is positioned to partially occlude one-half of the pupil of a normal incidence objective. In use, a probe beam is projected to fill the pupil of the objective. The portion of the incident probe beam that passes through the aperture is reduced in cross-sectional profile. As a result, after reflection by the sample, that portion of the probe beam underfills the non-occluded portion of the pupil. The remaining portion of the incident probe beam (i.e., the portion that passes through the non-occluded portion of the pupil) overfills the occluded pupil upon reflection from the sample. The combination of underfilling and overfilling reduces the sensitivity of the objective to tilting of the sample.

DETAILED DESCRIPTION OF THE PREFERRED EMBODIMENTS

Figure 1:
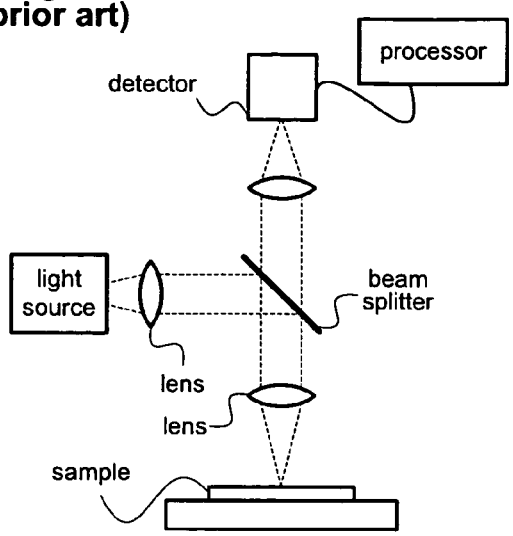
FIG. 1 shows a prior art optical metrology system.
Figure 2:
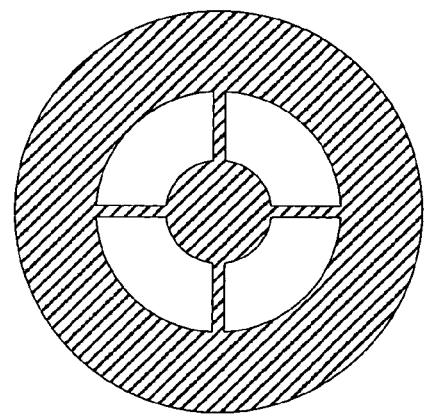
FIG. 2 is a schematic representation of the pupil of a prior art objective.
Figure 3:
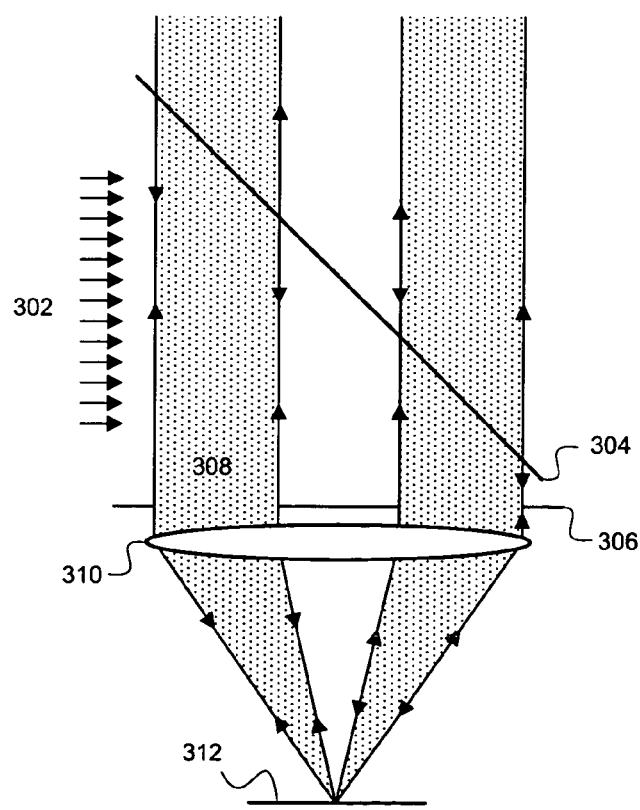
FIG. 3 is a schematic showing the path traveled by a probe beam as it is first focused by an objective onto a sample and then collected by the objective after reflection by the sample surface.
Figure 4A:
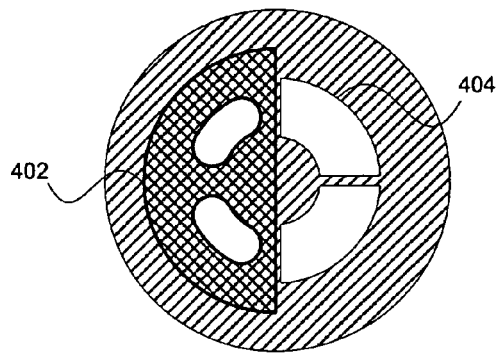
FIG. 4A shows an aperture for normal incidence Schwarzschild objectives as provided by an embodiment of the present invention.

The present invention includes an aperture for reducing tilt sensitivity in normal incidence optical metrology. FIG. 4A shows an implementation of the aperture 402 superimposed over a pupil 404 of a Schwarzschild objective. Aperture 402 is positioned to partially occlude one-half of pupil 404 and includes two holes. Each hole is slightly smaller than one of the non-obstructed quadrants of the Schwarzschild objective. The holes are internally radiused to minimize straight lines and sharp corners to help minimize the amount of diffracted light.

Figure 4B:
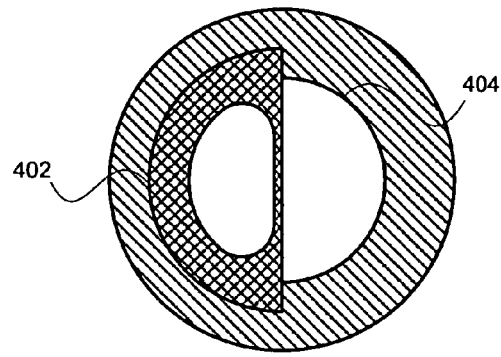
FIG. 4B shows an aperture for normal incidence refractive objectives as provided by an embodiment of the present invention.

FIG. 4B shows a second implementation of the aperture 402 superimposed over the pupil of a conventional objective (i.e., an objective without spiders or a central obstruction). Aperture 402 includes a single hole shaped as a compromise between minimizing diffraction effects and maximizing the total transmitted light. The optimal shape for the aperture for minimizing diffraction and reducing tilt sensitivity would be a circle having a diameter slightly smaller than half the diameter of the objective pupil.

Figure 5A:
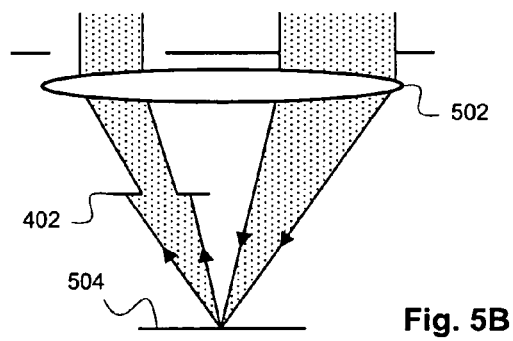
FIG. 5A shows attenuation of an incident probe beam within an optical metrology system by an aperture as provided by an embodiment of the present invention.

FIG. 5A shows the placement of aperture 402 between an objective 502 and a sample 504. This placement is unlike traditional apertures, which are typically placed in the back focal plane to avoid field vignetting. In this case, because of the particular geometry of aperture 402 and the small field size, vignetting is not a problem. It should also be noted that aperture 402, when appropriately sized may be located anywhere between sample 504 and the preceding beam splitter (not shown).

FIG. 5A shows only the light that enters the right-hand side of objective 502. This light is focused by objective 502 onto a sample 504. The beam reflecting from sample 504 falls on the aperture 402 which obstructs the outside edges of the beam. The remainder of the beam continues on through aperture 402 and past the left side of objective 502 without being further obstructed. In FIG. 5A, if sample 504 tilts slightly, the reflected beam will shift on the aperture 402 but (assuming that the beam is uniform), the amount of light passing through the aperture 402 will remain constant.

Figure 5B:
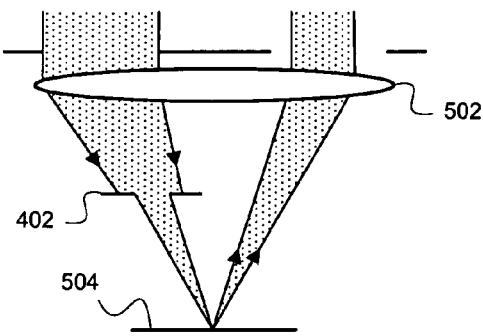
FIG. 5B shows attenuation of a reflected probe beam within an optical metrology system by an aperture as provided by an embodiment of the present invention.

FIG. 5B shows the light entering the left side objective 502 that was omitted for clarity from FIG. 5A. This light passes through objective 502 and falls on aperture 402. Aperture 402 attenuates the edges of the incident beam before it reaches sample 504. After being reflected by sample 504, the beam passes through aperture 402 and objective 502 with room to spare. If sample 504 tilts slightly, the beam will shift within objective 502, but will not be further attenuated. In this case the insensitivity to tilt does not depend on the beam uniformity.

As shown in FIGS. 5A and 5B, aperture 402 effectively reduces beam fluctuations associated with sample tilt. Importantly, by positioning aperture 402 between objective 502 and sample 504, it becomes possible to configure metrology systems to include distinctive apertures for different objectives. In multi-objective configurations, this allows each objective to be paired with an optimally configured aperture. Aperture 402 is easily retrofittable to existing metrology systems and has the additional advantage of reducing diffraction created by spider arm assemblies within Schwarzschild objectives.

Figure 6:
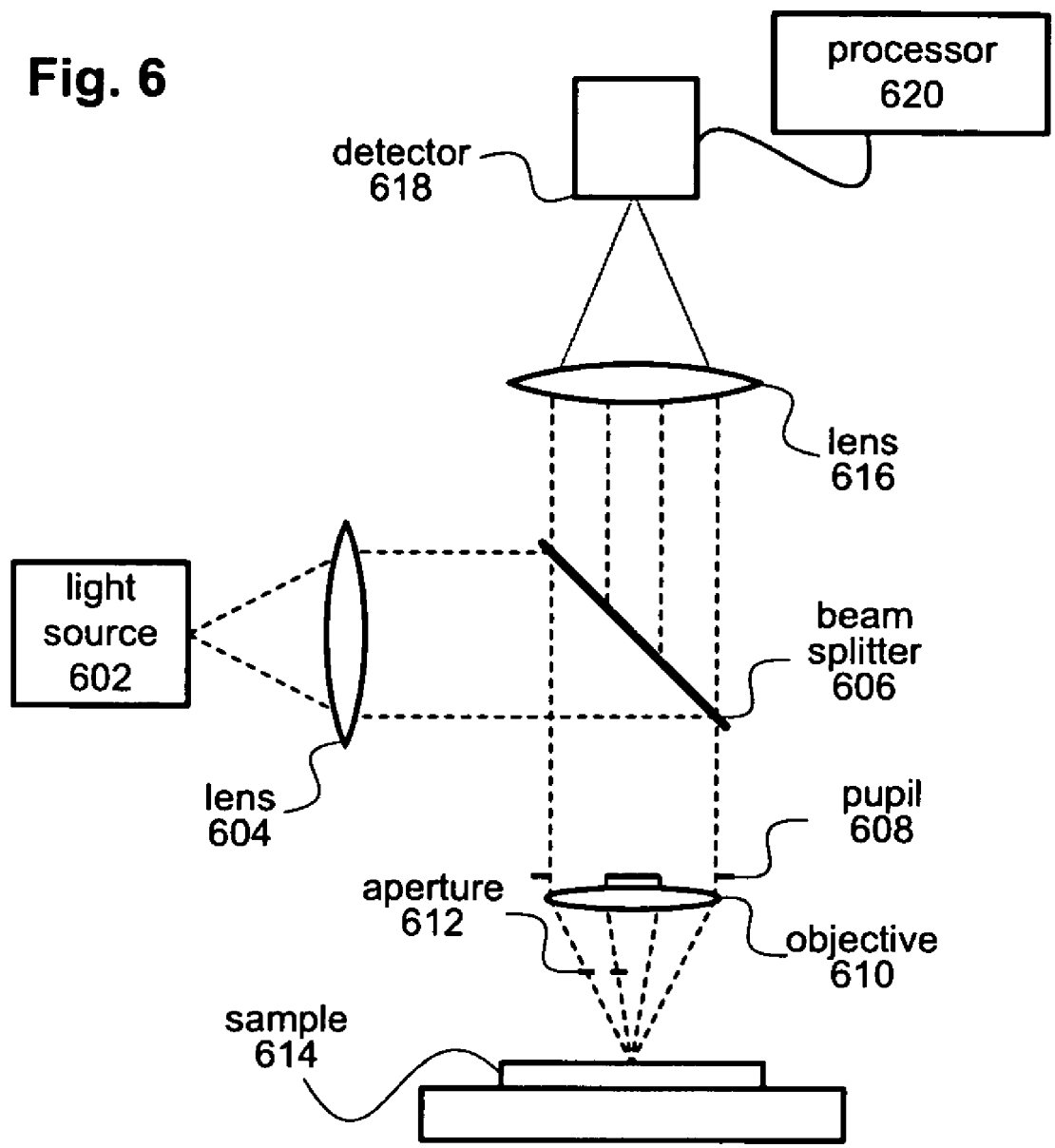
FIG. 6 shows a reflectometer implemented using an aperture as provided by an embodiment of the present invention.

FIG. 6 shows a reflectometer that includes the aperture provided by the present invention. As shown in FIG. 6, the reflectometer includes an illumination source 602 that creates a monochromatic or polychromatic probe beam. The probe beam is collimated by a lens 604 before reaching a beam splitter 606. Beam splitter 606 redirects the probe beam onto the pupil 608 of an objective lens 610. In general, it should be appreciated that pupil 608 is an abstraction shown for purposes of illustration and is not meant to imply a physical structure. Objective lens 610 may be of any type used in normal incidence reflectometry and may include multiple optical elements. As shown in FIG. 6, beam splitter 606 is positioned so that the redirected probe beam fills pupil 608. This is the preferred implementation where both pupil halves (shown in FIGS. 5A and 5B) are substantially or even fully illuminated.

Aperture 612 is placed between objective 610 and a sample 614. Aperture may be of the type shown in either FIG. 4A or 4B and may be positioned anywhere between beam splitter 606 and sample 614. Sample 614 reflects the probe beam back through objective lens 610 and beam splitter 606 to be focused by a lens 616 onto a detector 618. Detector converts the probe beam into corresponding signals for analysis by processor 620.

The use of aperture 612 makes the reflectometer of FIG. 6 less sensitive to sample tilt. This is accomplished while maintaining illumination to both pupil halves to maximize instrument sensitivity.

What is claimed is:

1. A method for optically inspecting and evaluating a sample, the method comprising:
   directing a probe beam towards an objective lens assembly, where the cross-sectional profile of the probe beam is large enough to substantially fill the pupil of the objective lens assembly;
   reducing the cross-sectional profile of the portion of the probe beam transmitted by a first half of the pupil; and
   gathering a reflection of the portion of the probe beam transmitted by the first half of the pupil through a second half of the pupil and gathering a reflection of the portion of the probe beam transmitted by the second half of the pupil through the first half of the pupil.

2. A method as recited in claim 1 in which the reducing step is performed using an aperture placed between the objective lens assembly and the sample.

3. A method as recited in claim 1 in which the directing step is performed using a partially reflective beam splitter.

4. A device for optically inspecting and evaluating a sample, the device comprising:
   an objective lens assembly;
   one or more optical components for directing a probe beam to substantially fill the pupil of the objective lens assembly; and
   an aperture positioned to partially occlude a first half of the pupil of the objective, the aperture reducing the cross-sectional profile of a portion of the probe beam that is projected through the first half of the pupil and collected by a second half of the pupil, the aperture also reducing the cross-sectional profile of a portion of the probe beam that is projected through the second half of the pupil and collected by the first halt of the pupil.

5. A device as recited in claim 4 an which the aperture is placed between the objective lens assembly and the sample.

6. A device as recited in claim 4 in which the one or more optical components include a partially reflective beam splitter.

7. A method for optically inspecting and evaluating a sample, the method comprising:

directing a probe beam to substantially fill the pupil of an objective lens assembly;

focusing the probe beam on the surface of the sample with the objective lens assembly;

partially obscuring a first half of the pupil of the objective lens assembly using an aperture placed between the objective lens assembly and the sample;

gathering the a reflected probe beam; and analyzing the reflected probe beam to evaluate the sample.

8. A method as recited in claim 7 in which the directing step is performed using a partially reflective beam splitter.

* * * * *